United States Patent [19]

Fenichel et al.

[11] 4,214,089

[45] Jul. 22, 1980

[54] THIAZOLO[3,2-A]BENZIMIDAZOLES, IMIDAZO [2,1-B]THIAZOLES, AND RELATED COMPOUNDS AS ANTINEOPLASTIC AGENTS, AND ENHANCERS OF THE IMMUNE RESPONSE

[75] Inventors: Richard L. Fenichel, Wyncote; Peter H. L. Wei, Springfield; Francis J. Gregory, Berwyn; Harvey E. Alburn, West Chester, all of Pa.

[73] Assignee: American Home Products Corporation, New York, N.Y.

[21] Appl. No.: 925,728

[22] Filed: Jul. 18, 1978

Related U.S. Application Data

[63] Continuation-in-part of Ser. No. 679,941, Apr. 26, 1976, abandoned, which is a continuation of Ser. No. 523,763, Nov. 14, 1974, abandoned.

[51] Int. Cl.$^2$ .......................................... C07D 277/24
[52] U.S. Cl. .................................. 548/151; 424/270; 544/252; 544/282; 548/329
[58] Field of Search ................................ 260/306.7 T

[56] References Cited

U.S. PATENT DOCUMENTS

| | | |
|---|---|---|
| 3,704,239 | 11/1972 | Wei et al. ................. 260/306.7 T |
| 3,853,872 | 11/1974 | Wei et al. ................. 260/306.7 T |
| 4,008,245 | 2/1977 | Acheson et al. ............ 260/306.7 T |

Primary Examiner—Donald G. Daus
Assistant Examiner—David B. Springer
Attorney, Agent, or Firm—Robert Wiser

[57] ABSTRACT

The use of 3-aryl-thiazolo[3,2-a]benzimidazoles, 3-aryl-imidazo[2,1-b]thiazoles, and related compounds as antineoplastic agents, and/or as enhancers of the immune response is disclosed.

2 Claims, No Drawings

THIAZOLO[3,2-A]BENZIMIDAZOLES, IMIDAZO [2,1-B]THIAZOLES, AND RELATED COMPOUNDS AS ANTINEOPLASTIC AGENTS, AND ENHANCERS OF THE IMMUNE RESPONSE

CROSS-REFERENCE TO RELATED APPLICATIONS

This application is a continuation-in-part of co-pending application Ser. No. 679,941, filed Apr. 26, 1976, abandoned, which is in turn a continuation of application Ser. No. 523,763, filed Nov. 14, 1974, now abandoned.

BACKGROUND OF THE INVENTION

The invention relates to the use of 3-aryl-thiazolo[3,2-a]benzimidazoles, 3-aryl-imidazo[2,1-b]thiazoles and structurally related compounds as antineoplastic agents and/or as enhancers of the immune response.

To suppress the growth and proliferation of neoplastic tissue in mammalian organisms radiation therapy and chemical therapy are frequently used as adjuncts to surgical removal of the neoplasm, and by themselves when surgery is not feasible or desirable.

The commonly used chemotherapeutic agents however, have a great deal of inherent cytotoxicity and thus are injurious to other tissues in the body as well as the neoplasm. They particularly affect rapidly proliferating cells and thus the body's immune response system is frequently affected and the organism's natural ability to resist infection and control the growth of immunologically incompatible cells impaired.

It has recently been reported to Nature New Biology, 240, 217 (1972), that 1-2,3,5,6-tetrahydro-6-phenyl-imidazo[2,1-b]thiazole (Levamisole) enhances the production of thymus lymphocytes (T-lymphocytes, thymocytes) and has the effect of suppressing metastases of Lewis Lung tumor implanted in mice. The present invention concerns the use of a series of compounds structurally different from Levamisole which have similar therapeutic properties.

SUMMARY OF THE INVENTION

The invention sought to be patented in its first principle process aspect resides in the concept of a process for inhibiting the growth of neoplastic tissue in a warm-blooded animal which comprises administering to a warm-blooded animal in need thereof, an effective amount of a compound of the formula:

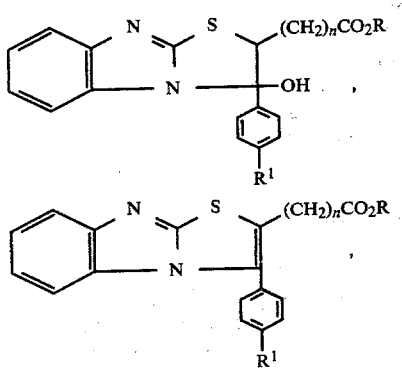

-continued

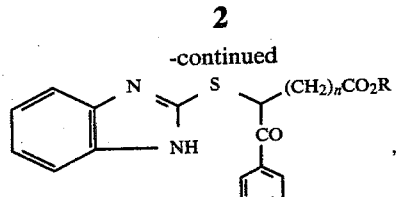

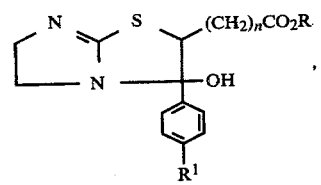

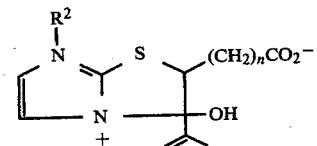

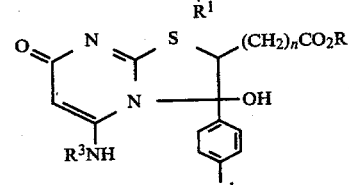

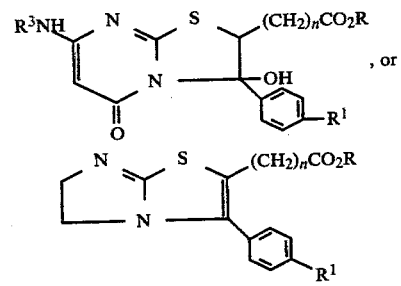

wherein R is hydrogen or lower alkyl of from 1 to about 4 carbon atoms; $R^1$ is hydrogen or halo; $R^2$ is lower alkyl; $R^3$ is lower alkanoyl of from 1 to about 6 carbon atoms; and n is the integer 1 or 2; and pharmaceutically acceptable addition salts thereof.

The invention sought to be patented in a first subgeneric process aspect of the first principle process aspect of the invention resides in the concept of a method for the inhibition of the growth of neoplastic tissue wherein metastases are suppressed which comprises administering to a warm-blooded animal in need thereof, an effective amount of a compound of the formulas A through H as defined hereinabove.

The invention sought to be patented in a second subgeneric process aspect of the first principle process aspect resides in the concept of a process for the inhibition of growth of neoplastic tissue which comprises administering to a warm-blooded animal in need thereof in conjunction with a cancer chemotherapeutic cytotoxic agent, an effective amount of a compound of the formulas A through H as defined hereinabove.

The invention sought to be patented in a second principle process aspect of the invention resides in the concept of a process for the enhancement of the immune response in a warm-blooded animal which comprises administering to a warm-blooded animal in need thereof, an effective amount of a compound of the formulas A through H as defined hereinabove.

The invention sought to be patented in its first composition aspect resides in the concept of a chemical compound having the structure:

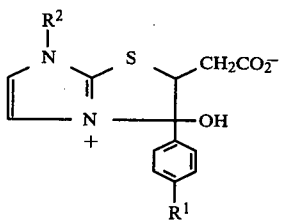

wherein $R^1$ and $R^2$ are as described hereinabove.

The tangible embodiments of the first composition aspect of the invention possess the inherent general physical properties of being crystalline solids, are substantially insoluble in water and are generally soluble in such polar solvents as dimethyl acetamide or acetonitrile. Examination of the products produced by the hereinafter described process reveals upon infrared and nuclear magnetic resonance spectral analysis, spectral data supporting the molecular structure herein set forth.

The tangible embodiments of the invention possess the inherent applied use characteristic of inhibiting the growth of neoplastic tissue, and enhancing the immune response in warm-blooded animals.

The invention sought to be patented in its second composition aspect resides in the concept of a chemical compound having the formula:

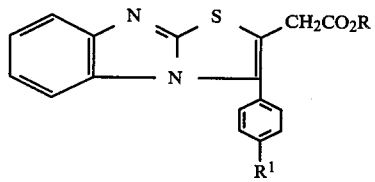

wherein R and $R^1$ are as defined hereinabove.

The tangible embodiments of the second composition aspect of the invention possess the inherent general physical properties of being crystalline solids, of being substantially insoluble in water, and soluble in such organic solvents as dimethyl acetamide, acetonitrile and the like. Examination of compounds produced according to the hereinafter described process reveals, upon infrared and nuclear magnetic resonance spectral analysis, spectral data supporting the molecular structure herein set forth.

The tangible embodiments of the second composition aspect of the invention possess the inherent applied use characteristics of inhibiting the growth of neoplastic tissue and enhancing the immune response in warm-blooded animals. These compounds are of special interest because of the low incidence of side-effects associated with their use, particularly their low thyrotoxic liability.

The invention sought to be patented in its third composition aspect resides in the concept of a pharmaceutical composition suitable for the inhibition of the growth of neoplastic tissue, or enhancement of the immune response which consists essentially of a compound of the formulas A through H as defined hereinabove, and a pharmaceutically acceptable carrier.

DESCRIPTION OF THE PREFERRED EMBODIMENTS

The compounds necessary for the practice of the process aspect of the invention are readily prepared. For example 5(7)-alkanoylamido-3-(substituted phenyl)-2,3-dihydro-3-hydroxy-7(5)-oxo-7(5)H-thiazolo[3,2-a]pyrimidine-2-acetic acids and their lower alkyl esters may be prepared by the procedure of U.S. Pat. No. 3,704,304, or a modification thereof which would be obvious to one skilled in the art, 3-(benzimidazol-2-ylthio)-3-(substituted benzoyl)-propionic acids and their lower alkyl esters and 2,3-dihydro-3-hydroxy-3-(substituted phenyl)-thiazolo[3,2-a]benzimidazole-2-acetic acids and their lower alkyl esters may be prepared by methods described in U.S. Pat. No. 3,704,239, 3-(substituted phenyl)-5,6-dihydroimidazo[2,1-b]thiazole-2-acetic acids, and their lower alkyl esters, and 3-(substituted phenyl)-2,3,5,6-tetrahydro-3-hydroxyimidazo[2,1-b]thiazole-2-acetic acids, and their alkyl esters may be prepared as described in copending application Ser. No. 383,455, filed May 24, 1973, 2-carboxymethyl-3(substituted phenyl)-2,3-dihydro-3-hydroxy-7-methyl-7H-imidazo[2,1-b]thiazolium hydroxide, inner salts are prepared by contacting the corresponding 3-(substituted benzoyl)-3-(1-methylimidazol-2-ylthio)propionic acid hydrobromide (Prepared by warming the corresponding 3-bromo-3-(substituted benzoyl)propionic acid and 2-mercapto-1-methylimidazole in glacial acetic acid) with water, and 3-(substituted phenyl)-thiazolo[3,2-a]benzimidazole-2-acetic acids and their lower alkyl esters may be prepared by warming, conveniently at reflux temperature the corresponding 2,3-dihydro-3-hydroxy compound as a suspension in an aqueous acid, dioxane mixture. The corresponding propionic acid derivatives may, if desired, be prepared by exactly the same procedures described above but substituting a methylene homolog of the appropriate starting material. The ester forms of the compositions required for the practice of the invention may also, if desired, be prepared from the corresponding free acids by standard methods.

The term pharmaceutically acceptable salts includes in addition to addition salts of pharmacologically-acceptable organic and inorganic acids such as hydrochloric, hydrobromic, sulfuric, nitric, phosphoric, methane sulfonic, benzene sulfonic, and the like; alkali metal carboxylates and carboxylates of a pharmacologically-acceptable cation derived from ammonia or a basic amine.

The alkali metal carboxylates of the invention can be prepared by mixing stoichiometrically equivalent amounts of the free acids, preferably in aqueous solution, with solutions of alkali metal bases, such as sodium potassium, and lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "lower alkyl" when used herein and in the appended claims includes straight and branched chain hydrocarbon radicals having from 1 to about 6 carbon atoms, illustrative members of which are methyl, ethyl, n-propyl, i-propyl, n-butyl, t-butyl, n-pentyl, n-hexyl, 3-methylpentyl, 2,3-dimethylbutyl, and the like.

The term "alkyl of from about 1 to about 4 carbon atoms" includes straight and branched chain hydrocarbon radicals, illustrative members of which are methyl, ethyl, n-propyl, i-propyl, n-butyl, t-butyl, and the like.

"Alkali metal" includes, for example, sodium, potassium, lithium, and like. "Halo" includes fluoro, chloro, bromo, and iodo. The term "lower alkanoyl of from 2 to about 6 carbon atoms" includes straight and branched chain aliphatic carboxylic acid radicals among which are acetic, propionic, i-butyric, n-hexanoic and the like. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

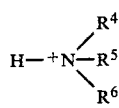

wherein $R^4$, $R^5$, and $R^6$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or when taken together with the nitrogen atom to which they are attached, any two of $R^4$, $R^5$, and $R^6$ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The term "cancer chemotherapeutic cytotoxic agent" when used herein and in the appended claims contemplates a member of the group of chemotherapeutic agents useful in the control of neoplastic tissue because of their ability to interfere with the proliferation of rapidly dividing cells. Among these are, for the purpose of illustration but without interfering with the generality of the foregoing, cyclophosphamide, 5-fluorouracil and methotrexate.

The term "pharmacologically acceptable carrier" contemplates usual and customary substances employed to formulate solid, oral unit dosages for pharmacological purposes, including in its broadest form animal feedstuff. It also includes those employed to formulate either in unit dose or multi dose form, oral and injectable suspensions and solutions, either directly or for reconstitution before administration.

To formulate dosages for administration according to this invention the active ingredient of Formulas A through H can be compounded into oral dosage forms such as tablets, capsules and the like. This is done by combining the active ingredients of Formulas A through H with conventional carriers, such as magnesium carbonate, magnesium stearate, talc, sugar, lactose, pectin, dextrin, starch, gelatin, tragacanth, methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases the proportion of active ingredients in said compositions both solid and liquid will be at least sufficient to impart antineoplastic and immunostimulant activity thereto on oral or parenteral administration.

In practicing the method of the invention, the instant compositions can be administered to warm-blooded animals, e.g. mice rats, rabbits, dogs, horses, monkeys, anthropoid apes, and the like, in a variety of dosage forms, alone or in combination with pharmacologically effective carriers, preferably orally or by injection.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the tangible embodiments of the invention are most desirably administered at a concentration level that will generally afford effective results without causing any harmful or deleterious side effects. With large animals (about 70 kg. body weight), for injection administration the dose is from about 10 milligrams to about 300 milligrams, and preferably from about 50 milligrams to about 150 milligrams per day, and for oral administration the dose is from about 50 milligrams to about 500 milligrams and preferably from about 100 milligrams to about 250 milligrams per day either as a single unit dose, or if desired, the dosage may be divided into convenient subunits administered at convenient times throughout the day.

The antineoplastic effect of the compositions of the invention may be demonstrated by standard pharmacological and histological procedures.

The pharmacological procedures which are described more fully in the examples given hereinafter are adapted from those generally described in Cancer Chemotherapy Reports, 25, (1962) pp. 1–59 as modified in Cancer Chemotherapy Reports, 3, No. 2, (1972) pp. 1–61. These procedures illustrate the ability of the compositions of the invention to suppress the growth of neoplastic tumor tissue either when administered singly or in combination with known cancer chemotherapeutic cytotoxic agents. The standard histological procedures which are described hereinbelow in the Examples illustrate the ability of the compositions of the invention to suppress the proliferation of metastases of neoplastic tumors as well as to retard the growth of the primary tumors themselves.

The ability of the compositions of inventions to enhance the immune response is illustrated by the enhanced ability of the compositions of the invention to retard the growth of neoplasms when the animals are predosed with the compositions as illustrated hereinbelow in the examples. The ability of the compositions of the invention to enhance the production of T lymphocytes also measures the ability of said compositions to enhance the immune response. The increase of the ability to form characteristic rosettes upon treatment of the separated white cells of blood of a treated animal with antigenic red cells, as illustrated hereinbelow in the examples, demonstrates enhancement of the immune response.

The following examples further illustrate the best mode contemplated by the inventors for carrying out their invention.

EXAMPLE 1

3-(p-Chlorophenyl)-Thiazolo[3,2-a]Benzimidazole-2-Acetic Acid 3-(p-Chlorophenyl)-2,3-dihydro-3-hydroxy-thiazolo[3,2-a]-benzimidazole-2-acetic acid, (5.0 g.) is suspended in a solution of 100 ml. of a 6 N NCl and 200 ml. of dioxane. The mixture is heated at reflux for 18 hours. The solution is concentrated in vacuo to 50 ml. To the concentrate is added 200 ml. of water, and sufficient 4 N NaOH solution to dissolve all the solids. The alkaline solution is made acidic with acetic acid. The solid is collected, washed well with water and air-dried. The crude material is recrystallized from dimethoxyethane. The product (2.0 g.) melts at 242°–243° C.

Analysis for: $C_{17}H_{11}ClN_2O_2S$: Calculated: C, 59.56; H, 3.24; Cl, 10.34; N, 8.17; S, 9.36: Found: C, 59,28; H, 3.40; Cl, 11.00; N, 8.03; S, 9.93.

EXAMPLE 2

To prepare: 3-phenyl-thiazolo[3,2-a]benzimidazole-2-acetic acid, treat 3-phenyl-2,3-dihydro-3-hydroxy-thiazolo[3,2-a]-benzimidazole-2-acetic acid as taught in Example 1.

EXAMPLE 3

To prepare: 3-[3-(p-bromophenyl)-thiazolo[3,2-a]benzimidazole-2-yl]-propionic acid, treat 3-[3-(p-bromophenyl)-2,3-dihydro-3-hydroxythiazolo[3,2-a]benzimidazole-2-yl]-propionic acid as taught in Example 1.

EXAMPLE 4

3-(p-Chlorobenzoyl)-3-(1-Methylimidazol-2-ylthio)Propionic Acid, Hydrobromide

A mixture of 3-bromo-3-(p-chlorobenzoyl)propionic acid (11.64 g., 0.04 m.) and 2-mercapto-1-methylimidazole (4.56 g., 0.04 m.) is dissolved in glacial acetic acid by warming on a steam bath. After filtration of a small amount of insoluble material the filtrate is evaporated. The residue is washed with ether and then treated with dimethoxyethane and the solid weighing 10 g. is collected. The crude material is recrystallized from acetonitrile. The pure compound melts at 173°–5°.

Analysis for: $C_{14}H_{13}ClN_2O_3S \cdot HBr$: Calculated: C, 41.44; H, 3.40; Br, 19.69; Cl, 8.74; N, 6.91; S, 7.90: Found: C, 41.81; H, 3.53; Br, 19.35; Cl, 8.58; N, 7.29; S, 8.08.

I.R. Analysis: $\lambda_{max}^{KBr}$ 3.7 (broad), 5.8, 5.95$\mu$.

NMR Analysis: Signals in DMSO at $\delta = 10.2$ (exchangeable), 7.9 (aromatic and vinyl H), 5.6 (C-H), 3.7 (N-CH$_3$), 3.2 (CH$_2$) ppm.

EXAMPLE 5

2-Carboxymethyl-3-(p-Chlorophenyl)-2,3-Dihydro-3-Hydroxy-7-Methyl-7H-Imidazo[2,1-b]Thiazolium Hydroxide, Inner Salt Finely ground 3-(p-chlorobenzoyl)-3-(1-methylimidazol-2-ylthio)propionic acid, hydrobromide, (6.0 g.) is added to 250 ml. of water and the mixture stirred for 20 min. The solid is collected and dried at room temperature. The crude material which weighs 4.6 g. and melts at 160°–2° is recrystallized from acetone. The recrystallized material melts at 161°–3°.

Analysis for: $C_{14}H_{13}ClN_2O_3S$: Calculated: C, 51.77; H, 4.03; Cl, 10.91; N, 8.63; S, 9.87: Found: C, 51.93; H, 4.18; Cl, 11.04; N, 8.66; S, 10.00.

I.R. Analysis: $\lambda_{max}^{KBr}$ 4.2, 5.2 (broad), 5.95 (sharp), 6.25$\mu$.

NMR Analysis: Signals in DMSO at $\delta = 7.8$ (aromatic quartet), 7.3 and 7.0 (vinyl protons), 5.2 (exchangeable), 3.3 (N-CH$_3$), 3.0 (CH$_2$) ppm.

EXAMPLE 6

To prepare: 4-(p-chlorobenzoyl)-4-(1-methylimidazol-2-ylthio)butyric acid, treat 4-bromo-4-(p-chlorobenzoyl)butyric acid and 2-mercapto-1-methylimidazole as taught in Example 4.

EXAMPLE 7

To prepare: 3-benzoyl-3-(1-propylimidazol-2-ylthio)-propionic acid, treat 3-bromo-3-benzoyl-propionic acid and 2-mercapto-1-propylimidazol as taught in Example 4.

EXAMPLE 8

To prepare: 2-carboxyethyl-3-(p-chlorophenyl)-2,3-dihydro-3-hydroxy-7-methyl-7H-imidazo[2,1-b]thiazolium hydroxide, inner salt treat 4-(p-chlorobenzoyl)-4-(1-methylimidazol-2-ylthio)butyric acid as taught in Example 5.

EXAMPLE 9

To prepare: 2-carboxymethyl-3-phenyl-2,3-dihydro-3-hydroxy-7-propyl-7H-imidazo[2,1-b]thiazolium hydroxide, inner salt, treat 3-benzoyl-3-(1-propylimidazol-2-ylthio)propionic acid as taught in Example 5.

EXAMPLE 10

Lewis Lung (3H) tumor fragments are implanted by trochar implant subcutaneously into the axillary region of BDF$_1$ mice of 20 g. body weight. The animals are dosed intraperitoneally with the test compound indicated below in the quantity per day specified for a period of 14 days. The animals are sacrificed on the fifteenth day and the number of animals which died during the test relative to the number of animals treated, (D/T), the mean weight of tumors in the group of treated animals relative to the mean tumor weight of the control animals, (T/C), the number of animals showing cures of the tumor, and the mean weight change for each group of animals is determined. When tested in this fashion a ratio of average tumor weights of treated animals to average tumor weights of controls of less than or equal to 42% is considered to indicate that the compound tested exhibits activity in retarding the growth of the implanted tumor at that dose level.

| Compound | Dose | D/T | % T/C | Cures | Wt. Chg. |
|---|---|---|---|---|---|
| 3-(p-chlorophenyl)-2,3-dihydro-3-hydroxythiazolo-[3,2-a]benzimidazole-2-acetic acid | 100 | 0/6 | 12 | 4 | +0.9 |
| cyclophosphamide | 20 | 2/6 | 15 | 2 | +0.6 |
| Control (Saline) | — | 0/18 | 1.38 g. tumor weight | 0 | +2.6 |

| Compound | Dose (mg/kg) | D/T | % T/C | Cures | Wt. Chg. |
|---|---|---|---|---|---|
| thiazole 3-(p-chlorophenyl)-thiazolo[3,2-a]benzimidazole-2-acetic acid | 100 | 1/10 | 41 | 2 | +2.0 |
| 3-(p-chlorophenyl)-5,6-dihydroimidazo[2,1-b]thiazole-2-acetic acid, ethyl ester | 200 | 1/10 | 29 | 3 | +0.4 |
| cyclophosphamide | 20 | 1/10 | 17 | 5 | 0 |
| controls (saline) | — | 1/10 | 1.38 tumor weight | 0 | +2.0 |

EXAMPLE 11

Following the procedure of Example 10, the BDF$_1$ rats are again treated at the dosages indicated with the compounds listed below with the results indicated.

| Compound | Dose (mg/kg) | D/T | % T/C | Cures | Wt. Chg. |
|---|---|---|---|---|---|
| 3-(p-chlorophenyl)-2,3-dihydro-3-hydroxythiazolo-[3,2-a]benzimidazole-2-acetic acid | 100 | 1/10 | 34 | 2 | +1.8 |
| 1-2,3,5,6-tetrahydro-6-phenyl-imidazo[2,1-b] | 25 | 1/10 | 79 | 0 | +0.9 |

EXAMPLE 12

Following the procedure described in Example 10, BDF$_1$ rats are treated at the doses indicated with the compounds listed below and with results as shown. For this test T/C results of 65% or less are considered indicative of activity.

| Compound | Dose | D/T | T/C |
|---|---|---|---|
| 3-(p-chlorophenyl)-2,3-dihydro-3-hydroxythiazolo-[3,2-a]benzimidazole-2-acetic acid | 150 | 0/9 | 70% |
| 2,3-dihydro-3-hydroxy-3-phenylthiazolo[3,2-a]benzimidazole-2-acetic acid, ethyl ester | 150 | 1/10 | 64% |
| 3-(benzimidazol-2-yl-thio)-3-(p-chlorobenzoyl)-propionic acid ethyl ester | 150 | 0/9 | 51% |
| 3-(p-chlorophenyl)-2,3-dihydro-3-hydroxythiazolo-[3,2-a]benzimidazole-2-acetic acid, ethyl ester | 150 | 4/10 | 79% |
| 3-(p-chlorobenzoyl)-3-(benzimidazol-2-ylthio)-propionic acid, methyl ester | 150 | 1/10 | 41% |
| 5-acetamido-3-(p-chlorophenyl)-2,3-dihydro-3-hydroxy-7-oxo-7H-thiazolo[3,2-a]pyrimidine-2-acetic acid, ethyl ester | 150 | 1/10 | 37% |
| cyclophosphamide | 20 | 0/5 | 18.5% |

EXAMPLE 13

Following the procedure described in Example 10 other BDF$_1$ mice are dosed at the levels indicated with the compounds listed below and the results shown are obtained. For the purposes of this series 60% or less T/C value is considered to indicate significant activity.

| Compound | Dose | D/T | T/C | Average wt. chg. |
|---|---|---|---|---|
| cyclophosphamide | 20 | 2/6 | 15 | +0.6 |
| 3-(p-chlorophenyl)-2,3-dihydro-3-hydroxythiazolo[3,2-a]benzimidazole-2-acetic acid | 100 | 0/6 | 12 | +0.9 |
| 3-(p-chlorophenyl)-2,3,5,6-tetrahydro-3-hydroxyimidazo[2,1-b]thiazole-2-acetic acid | 200 | 2/6 | 59 | −0.9 |
| 2,3,5,6-tetrahydro-3-hydroxy-3-phenyl-imidazo[2,1-b]thiazole-2-acetic acid ethyl ester | 200 | 0/6 | 158 | +0.5 |
| 3-(p-chlorophenyl)-5,6-dihydroimidazo-[2,1-b]thiazole-2-acetic acid, ethyl ester | 200 | 0/6 | 51 | +1.2 |
| 2-carboxymethyl-3-(p-chlorophenyl)-2,3-dihydro-3-hydroxy-7-methyl-7H-imidazo-[2,1-b]thiazolium hydroxide, inner salt | 100 | 0/6 | 54 | −0.1 |
| 3-(p-chlorophenyl)-2,3,5,6-tetrahydro-3-hydroxylimidazo[2,1-b]thiazole-2-acetic acid, ethyl ester | 100 | 0/6 | 82 | −1.3 |
| 3-(p-chlorophenyl)-2,3,6,7-tetrahydro-3-hydroxy-5H-thiazolo[3,2-a]pyrimidine-2-acetic acid | 100 | 0/6 | 90 | +0.2 |

-continued

| Compound | Dose | D/T | T/C | Average wt. chg. |
|---|---|---|---|---|
| control | — | 0/18 | 1.38 tumor wt. g. | +2.6 |

EXAMPLE 14

Following the procedure of Example 10 with the exception that the test was continued for 12 days, BDF$_1$ mice are treated, at the dosages indicated with the compounds listed below to obtain the results shown.

| Compound | Dose | D/T | T/C |
|---|---|---|---|
| 3-p-chlorophenyl-2,3-dihydro-3-hydroxythiazolo-[3,2-a]benzimidazole-2-acetic acid, ethyl ester | 12.5 | 0/10 | 66 |
| 3-(p-chlorophenyl)-2,3-dihydro-3-hydroxythiazolo-[3,2-a]benzimidazole-2-acetic acid, ethyl ester | 25 | 0/10 | 74 |
| 3-p-chlorophenyl-2,3-dihydro-3-hydroxythiazol-[3,2-a]benzimidazole-2-acetic acid, ethyl ester | 50 | 0/10 | 48 |
| 3-p-chlorophenyl-2,3-dihydro-3-hydroxythiazolo-[3,2-a]benzimidazole-2-acetic acid, ethyl ester | 100 | 2/10 | 47 |
| 3-p-chlorophenyl-2,3-dihydro-3-hydroxythiazolo-[3,2-a]benzimidazole-2-acetic acid, ethyl ester | 150 | 2/10 | 37 |
| 3-p-chlorophenyl-2,3-dihydro-3-hydroxythiazolo-[3,2-a]benzimidazole-2-acetic acid, ethyl ester | 200 | 9/9 | 67 |
| 1-2,3,5,6-tetrahydro-6-phenylimidazo[2,1-b]-thiazole | 12.5 | 0/10 | 78 |
| 1-2,3,5,6-tetrahydro-6-phenylimidazo[2,1-b]-thiazole | 25 | 4/10 | 69 |
| 1-2,3,5,6-tetrahydro-6-phenylimidazo[2,1-b]-thiazole | 50 | 4/9 | 65 |
| 1-2,3,5,6-tetrahydro-6-phenylimidazo[2,1-b]-thiazole | 100 | 10/10 | — |
| control | — | 0/20 | 2.5 tumor wt. g. |

EXAMPLE 15

Following the procedure of Example 10 except that animals are predosed for three days prior to insertion of the tumor and the animals are then treated for 10 days and sacrificed on the eleventh day after insertion of the tumor fragments. When treated at the dosages indicated of the compounds listed the results shown are obtained.

| Compound | Dose | D/T | T/C |
|---|---|---|---|
| 3-(p-chlorophenyl)-2,3-dihydro-3-hydroxythiazolo-[3,2-a]benzimidazole-2-acetic acid | 12.5 | 0/10 | 61 |
| 3-(p-chlorophenyl)-2,3-dihydro-3-hydroxythiazolo-[3,2-a]benzimidazole-2-acetic acid | 25 | 1/10 | 73 |
| 3-(p-chlorophenyl)-2,3-dihydro-3-hydroxythiazolo-[3,2-a]benzimidazole-2-acetic acid | 50 | 0/10 | 76 |
| 3-(p-chlorophenyl)2,3-dihydro-3-hydroxythiazolo-[3,2-a]benzimidazole-2-acetic acid | 100 | 1/10 | 58 |
| 3-(p-chlorophenyl)-2,3-dihydro-3-hydroxythiazolo-[3,2-a]benzimidazole-2-acetic acid | 150 | 1/10 | 81 |
| 3-(p-chlorophenyl)-2,3-dihydro-3-hydroxythiazolo-[3,2-a]benzimidazole-2-acetic acid | 200 | 1/10 | 50 |
| 1-2,3,5,6-tetrahydro-6-phenylimidazo[2,1-b]-thiazole | 12.5 | 1/10 | 113 |
| 1-2,3,5,6-tetrahydro-6-phenylimidazo[2,1-b]-thiazole | 25 | 2/10 | 82 |
| 1-2,3,5,6-tetrahydro-6-phenylimidazo[2,1-b]-thiazole | 50 | 5/10 | 124 |
| 1-2,3,5,6-tetrahydro-6-phenylimidazo[2,1-b]-thiazole | 100 | 10/10 | — |
| control | — | 0/20 | 2.16 gm. tumor wt. |

EXAMPLE 16

Following the procedure of Example 10 with the exception that the test was continued for 12 days the compounds listed below are administered to BDF$_1$ mice at the dosages indicated to obtain the results shown.

| Compound | Dose | D/T | T/C |
|---|---|---|---|
| 1. 3-(p-chlorophenyl)-2,3-dihydro-3-hydroxy-thiazolo[3,2-a]benzimidazole-2-acetic acid | 150 | 0/10 | 39 |
| 1 | 150 | | |

-continued

| Compound | Dose | D/T | T/C |
|---|---|---|---|
| plus | | 0/10 | 25 |
| 5-fluorouracil | 10 | | |
| 2. 1-2,3,5,6-tetrahydro-6-phenylimidazo-[2,1-b]thiazole | 25 | 1/10 | 36 |
| 2 | 25 | | |
| plus | | 1/10 | 36 |
| 5-fluorouracil | 10 | | |
| 5-fluorouracil | 10 | 0/10 | 53 |
| 1 | 150 | | |
| plus | | 3/10 | 57 |
| 2 | | | |
| controls | — | 1/20 | — |

EXAMPLE 17

Tissue cultures of a mouse mammary tumor virus (MMTV) cell strain are dispersed to single cells, washed with HBSS, adjusted to $1 \times 10^6$ cells/per ml. and 0.1 ml. inoculated subcutaneously into newborn hamsters. Newborn hamsters (1-4 day old and weighing approximately 3.0 gram each) are inoculated intraperitoneally (IP) with dilutions of 3-p-chlorophenyl-2,3-dihydro-3-hydroxythiazolo-[3,2-a]benzimidazole-2-acetic acid made in Saline-CMC (final concentration of 30%) at concentrations of 200, 150, 100 and 50 mg/kg/day. The compound is administered daily for 18 days in a volume of 0.1 ml./hamster. Rabbit anti-hamster lymphocytic serum obtained from Microbiological Associates, Inc., Bethesda, Md., is injected into all hamsters by the IP route on days 1 and 7 in a volume of 0.1 ml.

The results obtained are as indicated.

| Dose Mg/K/day | Hamster Litter No. | No. Hamsters with Tumors/ No. Infected | | | | Avg. Size of Tumors (mm) ($L \times W \times H$) | | | | | | |
|---|---|---|---|---|---|---|---|---|---|---|---|---|
| | | (day) 0 | 6-8 | 10-12 | 14-16 | (day) 0 | 8 | 10 | 12 | 15 | 17 |
| 200 | 1 | 0/11 | 1/11 | 4/11 | 10/10 | 0 | .19 | .05 | .15 | .6 | 1.79 |
| | 2 | 0/8 | 3/8 | 6/8 | 6/8 | 0 | .03 | .07 | .38 | .78 | 2.24 |
| 150 | 1 | 0/4 | ⅜ | ⅝ | ⅞ | 0 | .15 | .28 | .3 | 2.16 | 4.77 |
| | 2 | 0/11 | 6/11 | 10/11 | 10/11 | 0 | .2 | .5 | .63 | 2.2 | 2.19 |
| 100 | 1 | 0/11 | 6/11 | 9/11 | 11/11 | 0 | .04 | .14 | .32 | 1.25 | 2.02 |
| | 2 | 0/8 | 5/8 | 8/8 | — | 0 | .06 | .23 | .30 | 2.09 | 3.19 |
| 50 | 1 | 0/11 | 9/11 | 9/11 | 9/10 | 0 | .15 | .62 | .62 | 1.93 | 3.18 |
| | 2 | 0/7 | 5/7 | 7/7 | — | 0 | .14 | .15 | 1.4 | 3.29 | 5.4 |
| None | 1 | 0/10 | 10/10 | 10/10 | 10/10 | 0 | .13 | .4 | .86 | 2.5 | 3.5 |

Controls (No tumor injected)

| Dose Mg/K/day | Hamster Litter No. | No. Hamsters with Tumors/ No. Infected | |
|---|---|---|---|
| | | (day) 0 | 21 |
| 200 | 1 | 0/5 | 0/5 |
| 150 | 1 | 0/5 | 0/5 |
| 100 | 1 | 0/10 | 0/10 |
| 50 | 1 | 0/6 | 0/6 |

EXAMPLE 18

Following the procedure of Example 10 except that the experiment is continued for 16 days and where indicated the mice are pretreated with the compound administered for 3 days prior to insertion of the fragment of tumor tissue in their axillary regions. The results are as indicated.

| Compound | Dose | D/T | T/C |
|---|---|---|---|
| 3-(p-chlorophenyl)-2,3-dihydro-3-hydroxythiazolo[3,2-a]benzimidazole-2-acetic acid (predosed) | 100 | 1/10 | 49.2 |
| 3-(p-chlorophenyl)-2,3-dihydro-3-hydroxythiazolo[3,2-a]benzimidazole-2-acetic acid (predosed) | 150 | 0/10 | 35.4 |
| 3-(p-chlorophenyl)-2,3-dihydro-3-hydroxythiazolo[3,2-a]benzimidazole-2-acetic acid plus cyclophosphamide (predosed) | 150 20 | 1/10 | 2.9 |
| 3-(p-chlorophenyl)-2,3-dihydro-3-hydroxythiazolo[3,2-a]benzimidazole-2-acetic acid plus cyclophosphamide (predosed) | 150 10 | 0/10 | 34.2 |
| 3-(p-chlorophenyl)-2,3-dihydro-3-hydroxythiazolo[3,2-a]benzimidazole-2-acetic acid plus cyclophosphamide (predose) | 150 5 | 3/10 | 24.4 |
| 3-(p-chlorophenyl)-2,3-dihydro-3-hydroxythiazolo[3,2-a]benzimidazole-2-acetic acid plus cyclophosphamide (predose) | 150 1 | 2/10 | 55.6 |
| 3-(p-chlorophenyl)-2,3-dihydro-3-hydroxythiazolo[3,2-a]benzimidazole-2-acetic acid plus Freunds adj. (predose) | 150 0.1 ml. | 4/10 | 62.6 |
| Freunds adj. | 0.1 ml. | 1/10 | 85 |
| cyclophosphamide | 20 | 0/10 | 21.2 |
| cyclophosphamide | 10 | 0/10 | 53.8 |
| cyclophosphamide | 5 | 1/10 | 68.3 |
| cyclophosphamide | 1 | 1/10 | 50.3 |

EXAMPLE 19

BDF$_1$ mice are inoculated with Lewis Lung Tumor by trochar implant, treated with the experimental compound at the dosage indicated for 11 days followed by 4 days without treatment and the animals sacrificed on the 16th day after implantation. Samples of the tumor tissue and the lung tissue of the animals are subjected to gross and histological examination.

Animals are treated with 3-(p-chlorophenyl)-2,3-dihydro-3-hydroxythiazolo[3,2-a]benzimidazole-2-acetic acid (Compound 1) at 100 mg. per kg., per day, with 1-2,3,5,6-tetrahydro-6-phenyl-imidazo[2,1-b]thiazole (Compound 2) at 25 mg. per kg. per day, antithymocyte serum (ATS).

Specimens of masses at implantation sites consist in every case of viable, highly aggressive tumor. The tumor is composed of large cells with abundant cytoplasm and large pleomorphic nuclei which exhibit numerous mitotic figures. There is aggressive invasion of contiguous subcutaneous connective tissues and muscle. The cells are closely packed together and the blood supply of the tumor is rather limited, with central areas of necrosis occurring, probably due to lack of blood supply. The appearance of primary tumor is essentially the same in the three experimental groups examined histologically. No morphologic basis is found for the significantly lower tumor weights of mice treated with Compound 1.

EXAMPLE 20

Groups of $BDF_1$ mice are inoculated with Lewis Lung Tumor in the axillary region by trochar implant. The mice are treated with the test compounds indicated and in addition to groups of animals receiving each of the test compounds 0.1 ml. of antithymocyte serum (ATS) is administered 1 day before implant, 1 and 5 days after implantation for the first week and twice a week for the remainder of the experiment. At the end of the two-week period, the mice receive no treatment for

| TREATMENT | MOUSE NO. | GROSS OBSERVATIONS | MICROSCOPIC OBSERVATIONS |
|---|---|---|---|
| Cpd. 1 - 100 mpk | 2 | No tumors | Several tiny subpleural tumor metastases which have elevated the pleura. Also, a tiny focus deeper within the parenchyma. In the latter there are tumor emboli in pulmonary blood vessels and also in peribronchiolar lymphatics. |
| Cpd. 1 - 100 mpk | 3 | No tumors | No visible lung tumors |
| Cpd. 1 - 100 mpk | 4 | No tumors | Several small tumor foci seen. Tumor cells are confined to endothelium and adventitial zones of medium sized pulmonary blood vessels and there is an intense mixed inflammatory reaction in areas where neoplastic cells are visible. Many lymphocytes and plasma cells are present in the inflammatory infiltrate |
| Cpd. 1 - 100 mpk | 5 | No tumors | Some very tiny, early metastases visible within small blood vessels are peribronchiolar lymphatics |
| Cpd. 1 - 100 mpk | 9 | No tumors. One entire lobe appears consolidated | Sections of the consolidated lobe shows advanced consolidation of the entire lobe with an extremely prominent plasma cell reaction around bronchioles and large blood vessels. Sections of lobes which appeared grossly normal showed a number of very early, tiny metastases-mostly present within peribronchiolar or perivascular lymphatics. In addition a sizable area of chronic interstitial pneumonitis with epithelialization of alveolar lining cells was visible. This appeared to be unassociated with the presence of tumor. |
| Cpd. 1 - 100 mpk | 6,7,8 | 16 atypical areas were observed. Were considered grossly not to be tumor. 10 areas of atypical lesions were observed. 4 atypical areas observed. | In each of these cases multiple tumor foci were seen in lung sections. Metastasis was both by lymphatic and hematogenous routes, tumor being visible within peribronchiolar and perivascular lymphatics as well as within the lumina of sizable pulmonary blood vessel. |
| Cpd. 2 - 25 mpk | 2 | No tumors | Several tiny early metastases seen |
| Cpd. 2 - 25 mpk | 5 | 6 tumors observed | One sizable tumor metastasis observed in several sections |
| Cpd. 2 - 25 mpk | 8 | No tumors | Two very small tumor foci observed |
| Cpd. 2 - 25 mpk | 9 | No tumors | No metastases observed |
| Controls - A. T. S. | 1 | 5 tumors observed | Multiple large metastases observed |
| Controls - A. T. S. | 2 | 8 tumors observed | Multiple large metastases observed |
| Controls - A. T. S. | 3 | 10 tumors observed | Multiple small metastases observed | four days before sacrificing. A comparative control group receiving each of the test compounds without ATS treatment is run concurrently. The results obtained are as follows.

| Compound | Dose mg/kg. | ATS | Tumor Wt. gms. | D/T | T/C | Av. No. Lung Metastases | |
|---|---|---|---|---|---|---|---|
| | | | | | | Dorsal Surface | Entire Lung |
| 3-(p-chlorophenyl)-2,3-dihydro-3-hydroxythiazolo-[3,2-a]benzimidazole-2-acetic acid | 100 | no | 1.98 | 1/10 | 41 | 0.4 | 2.4 |
| 3-(p-chlorophenyl)-2,3-dihydro-3-hydroxythiazolo-[3,2-a]benzimidazole-2-acetic acid | 100 | yes | 1.98 | 4/10 | 41 | 5.3 | 6.3 |
| 1-2,3,5,6-tetrahydro-6-phenyl-imidazo[2,1-b]-thiazole | 25 | no | 2.54 | 2/10 | 53 | — | 3.4 |
| 1-2,3,5,6-tetrahydro-6-phenyl-imidazo[2,1-b]-thiazole | 25 | yes | 1.92 | 6/10 | 40 | 1.5 | 2.5 |
| cyclophosphamide | 20 | no | 1.01 | 0/9 | 21 | 0 | 0 |
| cyclophosphamide | 20 | yes | 0.21 | 9/10 | — | 2.0 | 6.0 |

-continued

| Compound | Dose mg/kg. | ATS | Tumor Wt. gms. | D/T | T/C | Av. No. Lung Metastases | |
|---|---|---|---|---|---|---|---|
| | | | | | | Dorsal Surface | Entire Lung |
| Saline | — | no | 4.39 | 0/10 | — | 4.7 | 12.0 |
| Saline | — | yes | 3.02 | 2/10 | — | 7.5 | 17.5 |

EXAMPLE 21

A. A modified Hanks Balanced Salt Solution (MHBSS) is prepared as follows:

| Stock solution | | |
|---|---|---|
| NaCl | 75 | g. |
| K CL | 7.5 | |
| Na₂HPO₄ | 1.0 | |
| KH₂PO₄ | 1.2 | |
| K₂HPO₄ | 5.0 | |
| deionized water to make | 1 | liter |
| MHBSS | | |
| Above stock solution | 10 | ml. |
| 1% Na₂HPO₄ solution | 7 | ml. |
| deionized water to make | 100 | ml. |

B. Fasted male rats are given single oral doses of the test compound. After 18 hours 5 ml. of blood is withdrawn with a heparinized syringe, and diluted 1:1 with MHBSS. 8 ml. of diluted blood is layered on 4 ml. of gradient prepared from 10 parts of 50% Hypaque and 16 parts of 2% methyl cellulose and then centrifuged at about 1200 RPM for 20 minutes. The white cell layer is removed and washed 2 or 3 times with MHBSS centrifuging at about 2000 RPM for 5 minutes.

C. Guinea pig blood is obtained as described above in part B for the withdrawal of rat blood. This blood is washed twice with MHBSS and physiological saline pH 7.4 in a 0.1 ml. to 10 ml. ratio as described above for part B for the separated white cells.

D. 0.1 ml. of rat white cell suspension at a concentration of $1.6 \times 10^6$ cells per ml. in MHBSS, 0.1 ml. of guinea pig red blood cells at a concentration of $6.4 \times 10^6$ cells per ml. in tris-saline solution, and 0.1 ml. of fetal calf serum in MHBSS (1:1) are mixed and incubated at 37° C. for 1 hour then mixed gently and 1 drop is counted for ratio of rosettes per 100 white blood cells. 3 groups of 100 cells for each of experimental and control groups to determine average number of rosettes per 100 white blood cells and to compute the ratio of rosettes in white cells from treated blood to those from control blood. The results are as shown.

| Compound | Dose (mg/kg) | Rosette Formation Ratio (Exp/Control) |
|---|---|---|
| 3-(p-chlorophenyl)-2,3-dihydro-3-hydroxythiazolo[3,2-a]benzimidazole-2-acetic acid | 100 | 1.90 |
| 3-(p-chlorophenyl)-2,3-dihydro-3-hydroxythiazolo[3,2-a]benzimidazole-2-acetic acid | 25 | 0.80 |
| 3-(p-chlorophenyl)-2,3-dihydro-3-hydroxythiazolo[3,2-a]benzimidazole-2-acetic acid | 50 | 1.20 |
| 3-(p-chlorophenyl)2,3-dihydro-3-hydroxythiazolo[3,2-a]benzimidazole-2-acetic acid | 75 | 1.33 |
| 3-(p-chlorophenyl)-2,3-dihydro-3-hydroxythiazolo[3,2-a]benzimidazole-2-acetic acid (2 doses - 1/day) | 75 (150 total) | 2.02 |
| 3-(p-chlorophenyl)-2,3-dihydro-3-hydroxythiazolo[3,2-a]benzimidazole-2-acetic acid (2 doses - 1/day) | 150 (300 total) | 2.67 |
| 1-2,3,5,6-tetrahydro-6-phenylimidazo[2,1-b]thiazole | 25 | 0.60 |
| 1-2,3,5,6-tetrahydro-6-phenylimidazo[2,1-b]thiazole | 50 | 0.80 |
| 1-2,3,5,6-tetrahydro-6-phenylimidazo[2,1-b]thiazole | 75 | 1.33 |
| 1-2,3,5,6-tetrahydro-6-phenylimidazo[2,1-b]thiazole | 100 (200 total) | 1.94 |

EXAMPLE 22

Following the procedure of Example 21 except that in all cases rats receive doses of test compound of 2 consecutive days and blood is sampled on the third day, and comparison is made between intact and thymectomized litter mates the Exp./control ratios shown on administration of the dosages indicated of 3-(p-chlorophenyl)-2,3-dihydro-3-hydroxythiazolo[3,2-a]benzimidazole-2-acetic acid are obtained.

| Dose | Exp./Cont. (Thymectomized) | Exp./Cont. (Intact) |
|---|---|---|
| 75 | 0 | 0 |
| 100 | 0.3 | 2.6 |
| 150 | hemolyzed | 3.6 |

EXAMPLE 23

A tablet for use in the suppression of the growth of neoplastic tissue or enhancement of the immune response consists of the following ingredients:

| | mg. |
|---|---|
| 3-(p-chlorophenyl)-2,3-dihydro-3-hydroxythiazolo[3,2-a]benzimidazole-2-acetic acid | 150 |
| carboxymethyl cellulose | 15 |
| lactose powder | 25 |
| redried corn starch | 25 |
| magnesium stearate powder | 4 |
| calcium silicate powder q. s. | 400 |

EXAMPLE 24

A suspension for parenteral use for the supression of the growth of neoplastic tissue or enhancing of the immune response consists of the following ingredients per cc.:

| | mg. |
|---|---|
| 3-(p-chlorophenyl)-2,3-dihydro-3-hydroxythiazolo[3,2-a]benzimidazole-2-acetic acid | 150 |

|  | mg. |
| --- | --- |
| benzyl alcohol | 10.0 |
| sodium chloride | 90.0 |
| polyoxyethylene sorbitan monooleate | 4.0 |
| sodium carboxymethyl cellulose | 5.0 |
| water for injection | q.s. |

EXAMPLE 25

A tablet for oral administration in suppressing the growth of neoplastic tissue or enhancing the immune response is prepared using the proportions of ingredients of Example 23 but substituting for 3-(p-chlorophenyl)-2,3-dihydro-3-hydroxythiazolo-[3,2-a]benzimidazole-2-acetic acid the following compositions: 3-(p-chlorophenyl)-thiazolo[3,2-a]benzimidazole-2-acetic acid; 3-(p-chlorophenyl)-5,6-dihydroimidazo[2,1-b]thiazole-2-acetic acid, ethyl ester; 2,3-dihydro-3-hydroxy-3-phenylthiazolo[3,2-a]benzimidazole-2-acetic acid, ethyl ester; 3-(benzimidazole-2-yl-thio)-3-(p-chlorobenzoyl)-propionic acid, ethyl ester; 3-(p-chlorobenzoyl)-3-(benzimidazole-2-ylthio)-propionic acid, methyl ester; 5-acetamido-3-(p-chlorophenyl)-2,3-dihydro-3-hydroxy-7-oxo-7H-thiazolo-[3,2-a]pyrimidine-2-acetic acid, ethyl ester; 3-(p-chlorophenyl)-2,3,5,6-tetrahydro-3-hydroxyimidazo[2,1-b]thiazole-2-acetic acid ethyl ester; 2-carboxymethyl-3-(p-chlorophenyl)-2,3-dihydro-3-hydroxy-7-methyl-7H-imidazo[2,1-b]thiazolium hydroxide, inner salt.

EXAMPLE 26

A suspension is prepared for parenteral administration in suppressing the growth of neoplastic tissue or enhancement of the immune response but substituting for 3-(p-chlorophenyl)-2,3-dihydro-3-hydroxythiazolo[3,2-a]benzimidazole-2-acetic acid the following compositions: 3-(p-chlorophenyl)-thiazolo[3,2-a]benzimidazole-2-acetic acid; 3-(p-chlorophenyl)-5,6-dihydroimidazo[2,1-b]thiazole-2-acetic acid, ethyl ester; 2,3-dihydro-3-hydroxy-3-phenylthiazolo-[3,2-a]benzimidazole-2-acetic acid, ethyl ester; 3-(benzimidazole-2-yl-thio)-3-(p-chlorobenzoyl)-propionic acid, ethyl ester; 3-(p-chlorobenzoyl)-3-(benzimidazole-2-ylthio)-propionic acid, methyl ester; 5-acetamido-3-(p-chlorophenyl)-2,3-dihydro-3-hydroxy-7-oxo-7H-thiazolo[3,2-a]pyrimidine-2-acetic acid, ethyl ester; 3-(p-chlorophenyl)-2,3,5,6-tetrahydro-3-hydroxyimidazo[2,1-b]thiazole-2-acetic acid ethyl ester; 2-carboxymethyl-3-(p-chlorophenyl)-2,3-dihydro-3-hydroxy-7-methyl-7H-imidazo[2,1-b]thiazolium hydroxide, inner salt.

The subject matter which the applicants regard as their invention is particularly pointed out and distinctly claimed as follows:

1. A chemical compound having the structure:

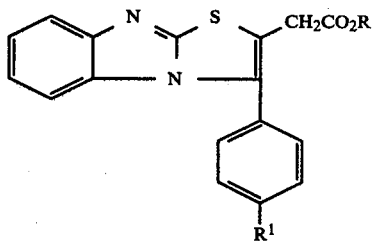

wherein R is hydrogen or lower alkyl of from 1 to 4 carbon atoms; and $R^1$ is chloro; and the pharmaceutically acceptable salts thereof.

2. A compound as defined in claim 1 which is 3-(p-chlorophenyl)-thiazolo[3,2-a]benzimidazole-2-acetic acid.

* * * * *